United States Patent [19]

Jessamine et al.

[11] Patent Number: 4,903,710
[45] Date of Patent: Feb. 27, 1990

[54] SURGICAL ISOLATION DRAPES

[76] Inventors: John G. Jessamine, 34 Waterloo Road, Workingham, Berkshire, RG11 2JH, United Kingdom; Martin Taube, 21 Swiss Valley, Lianelli, Dyfed, Wales

[21] Appl. No.: 141,475

[22] Filed: Jan. 5, 1988

[30] Foreign Application Priority Data

Jan. 6, 1987 [GB] United Kingdom ............... 8700160

[51] Int. Cl.⁴ ............................................. A61F 13/00
[52] U.S. Cl. ..................................... 128/849; 128/846; 128/852
[58] Field of Search ................. 128/1 R, 1 B, 132 D, 128/132 R, 205.26, 846, 849, 850, 851, 852, 853, 854, 855, 856

[56] References Cited

U.S. PATENT DOCUMENTS

| | | | |
|---|---|---|---|
| 1,554,692 | 9/1925 | Shane | 128/132 D |
| 3,051,164 | 8/1962 | Trexler | 128/1 B |
| 3,251,360 | 5/1966 | Melges | 128/132 D |
| 3,272,199 | 9/1966 | Matthews | 128/1 R |
| 4,007,741 | 2/1977 | Waldrop et al. | 128/132 R |
| 4,069,913 | 1/1978 | Harrigan | 128/132 R |
| 4,366,809 | 1/1983 | Trexler | 128/205.26 |
| 4,367,728 | 1/1983 | Mutke | 128/132 R |
| 4,414,968 | 11/1983 | Amin | 128/132 D |
| 4,690,137 | 9/1987 | Starzmann | 128/132 D |

Primary Examiner—Robert A. Hafer
Assistant Examiner—Sam Rimell
Attorney, Agent, or Firm—Jacobs & Jacobs

[57] ABSTRACT

A surgical isolation drape for use in urological, gynaecological or proctorlogical surgical procedures or examination of patients comprises a sheet (10) of flexible transparent or translucent plastics material provided with adhesive strips (13, 14) and/or tapes (131, 141) for attaching the upper end of the sheet to the patient's legs so that the remainder of the sheet hangs down therefrom. The lower portion of the sheet is formed into a funnel (30) either by seaming its edge portions (221, 231) together or by means of attachment means such as tapes (15 to 20) for joining the sides of the lower part of the sheet. A central part of the sheet is provided with apertures (24, 25) sealed by flexible members such as surgical gloves (26, 27) which permit passage of the surgeon's hands. For urological use, the central portion also ha a sealable aperture (28) permitting ocular access to the lens of a urological instrument and a support for the lens casing, e.g. a reinforcing ring (29) and a box (34) or sheet (36) attached to the sheet (10). A self-adhesive flap (41) may also be used to protect the lens. For gynaecological use, the aperture (28) is replaced by a sealed inspection window.

13 Claims, 8 Drawing Sheets

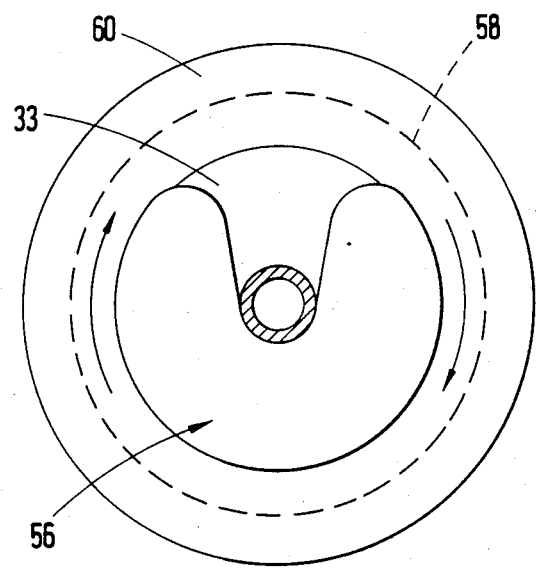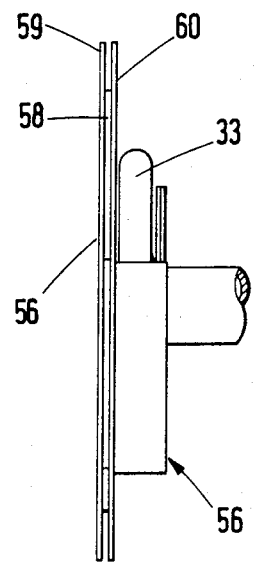
Fig. 14  Fig. 15
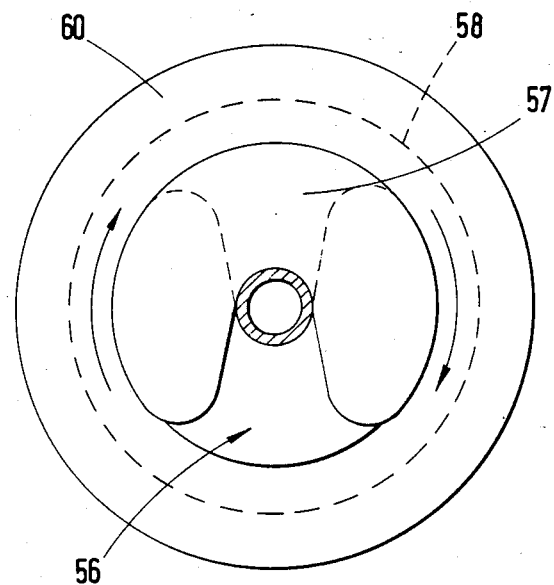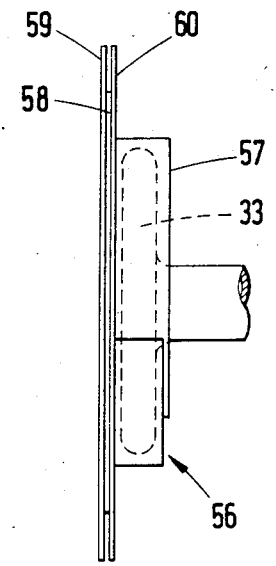
Fig. 16  Fig. 17

SURGICAL ISOLATION DRAPES

This invention relates to surgical isolation drapes, and more specifically to surgical drapes for use in urological, gynaecological or proctorlogical surgical procedures or examination of patients.

Known plastic drapes for use in surgical procedures are designed primarily to provide a barrier against infection to a surgical incision from adjacent potential sources of infection. In the urological field, one such drape has been designed to incorporate a central inspection aperture to accommodate the genitalia and a finger cot below to permit rectal access. A disadvantage of such known drapes is that the surgeon performing the examination is not protected from body fluids which may emanate from the patient. In the current climate of anxiety concerning AIDS (acquired immune deficiency syndrome) this may be considered by surgeons to represent an unacceptable health risk, as well as being unpleasant and insanitary.

The object of the invention is to provide a surgical drape for use in urological or gynaecological examinations or operations which will isolate the surgeon from the patient's body fluids and enable the examination to be made conveniently and in a cleaner environment.

According to the present invention, a surgical drape for use in urological, gynaecological or protorlogical surgical procedures or examination of patients comprises a sheet of flexible transparent or translucent plastics material, one end of the sheet being provided with means for attaching the sheet to the patients legs, so that the remainder of the sheet hangs down therefrom, the sides of the sheet adjacent to the opposite or lower end of the sheet being joined, or provided with attachment means to enable them to be joined, to form the said lower part of the sheet into a funnel, and a central part of the sheet being provided with apertures sealed by flexible members which permit passage of the surgeon's hands.

In the case where the surgical drape is to be used for urological examination, its central portion will generally also be provided with a sealable aperture permitting ocular access to the lens of a urological instrument. Preferably the central portion of the sheet has attached to it, around the sealable aperture, a support for the lens casing of the urological instrument. The support may be shaped to receive and locate the lens casing.

In an alternative case where the surgical drape is for use in gynaecological examination, its central portion will generally be provided with a highly transparent inspection window.

In either case, the flexible members permitting passage of the surgeon's hands are preferably gloves sealed to the sheet around each aperture. As an alternative, the flexible members may be elasticated membranes sealed to the sheet around each aperture.

Specific embodiments of the invention will now be described in more detail by way of example, with reference to the accompanying drawings, in which.

Figure 12:
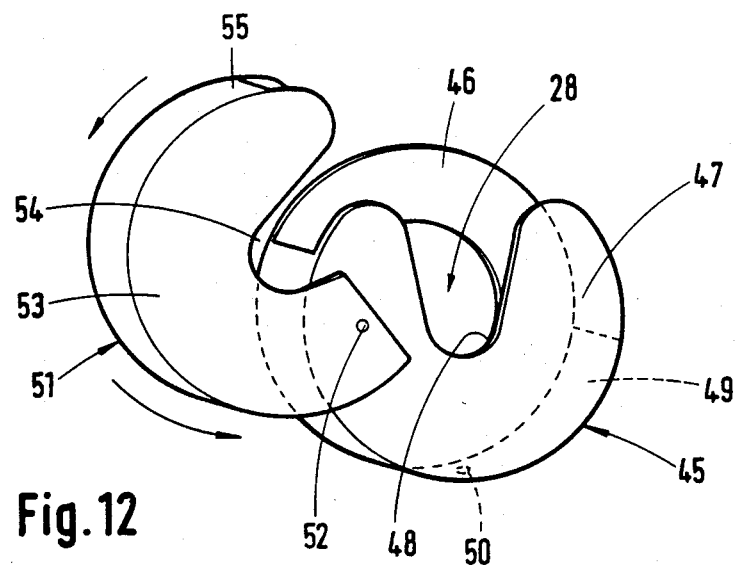
Figure 13:
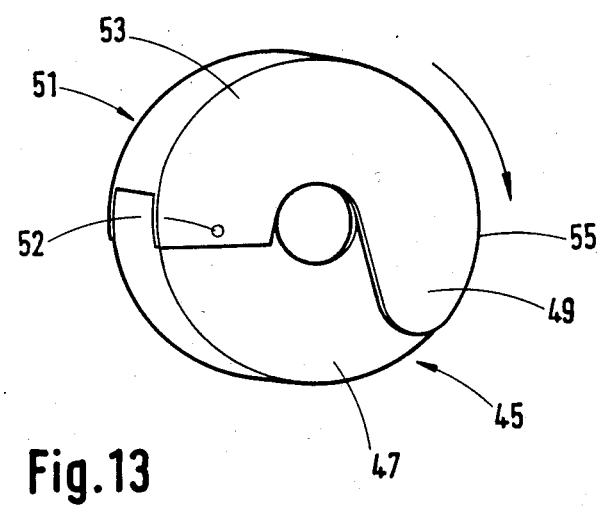

FIG. 12 and 13 are perspective views of an alternative form of support, shown in two different positions, for the lens of a urological instrument, FIG. 14 and 15 are a perspective view and side view, respectively, of a third form of lens support in the open position, and FIG. 16 and 17 are a perspective view and side view of the third form of lens support in the closed position.

Figure 1:
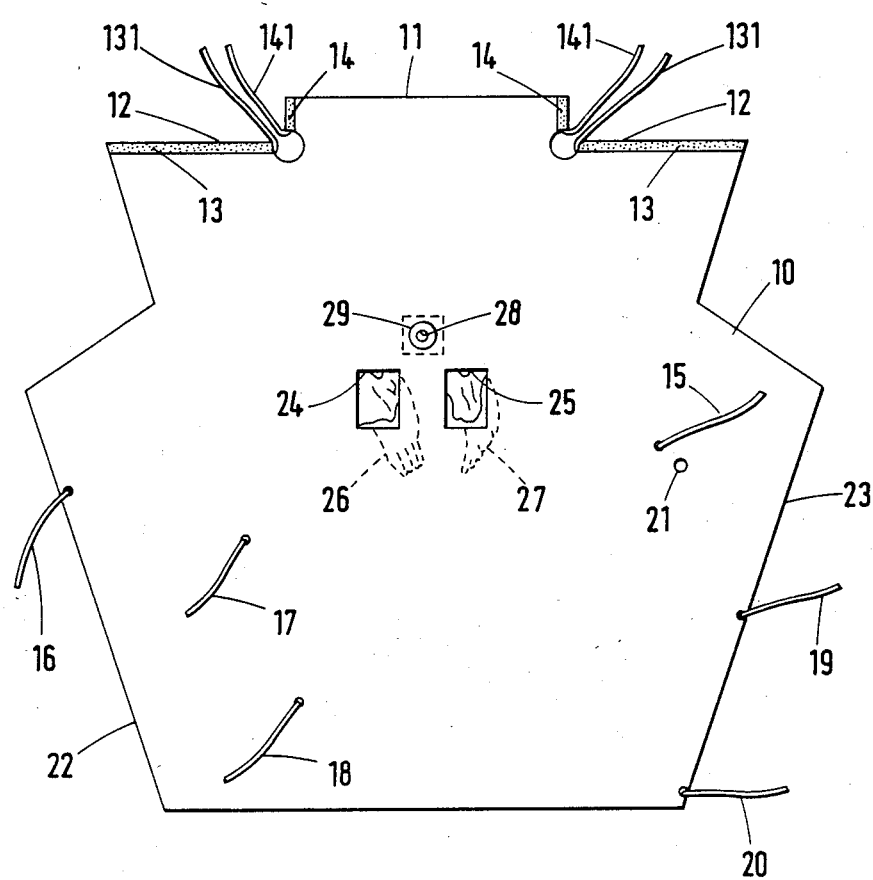
FIG. 1 is a view of a first form of surgical drape laid out flat.

In the embodiment illustrated in FIG. 1; the surgical drape according to the invention comprises a sheet 10 of strong but flexible transparent plastics material. Its upper edge 11 is formed at each side with stepped portions 12, provided with self-adhesive strips 13, 14 and with tape 131, 141 to enable these portions to be attached to a patient's legs. Attachment means in the form of tapes 15, 16, 17, 18, 19, 20 are attached to the sheet 10 as shown, and a hole 21 is provided adjacent to the attachment point of tape 15, for cooperating with tape 16, so as to enable the sides 22, 23 of the sheet 10 to be joined to one another so as to form the lower part of the sheet 10 into a funnel.

The central part of the sheet 10 is provided with a pair of apertures 24, 25 sealed around their peripheries by being attached to respective surgical gloves 26, 27 on the patient's side of the drape.

The central portion of the sheet 10 is also provided with an aperture 28 permitting the surgeon to apply his eye to the lens of a urological instrument, such as a cystoscope, on the patient's side of the drape. A reinforcing ring 29 surrounds the aperture 28 and sealing means are provided as described below to enable the aperture 28 to be sealed in use.

Figure 2:
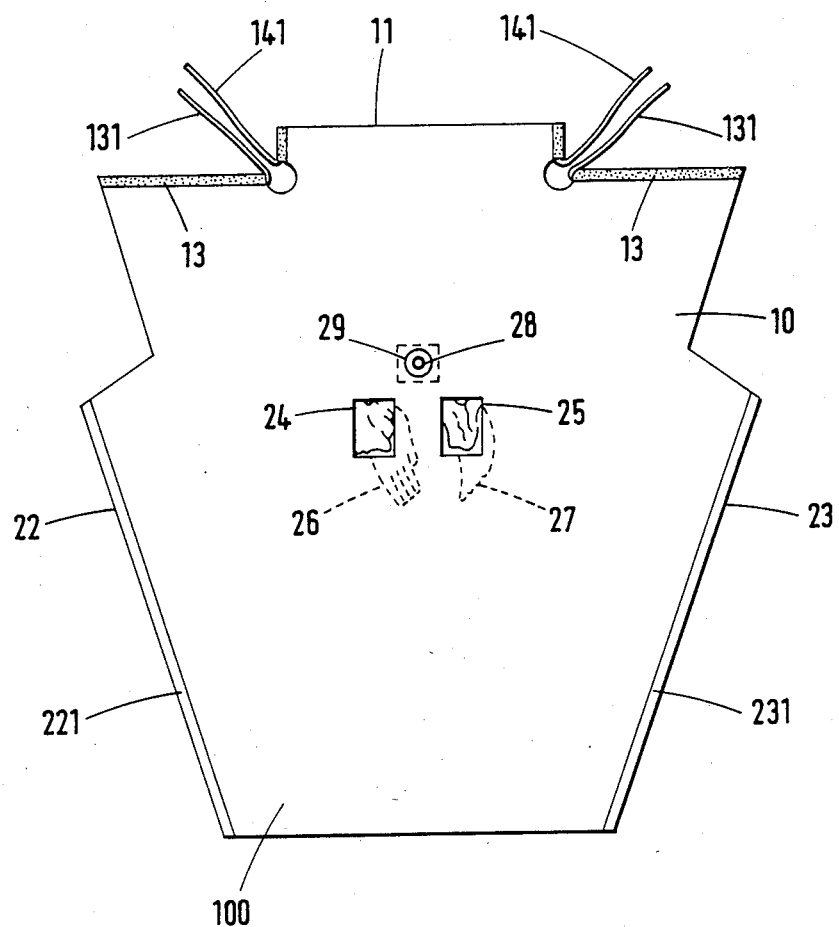
FIG. 2 is a similar view of a second form of surgical drape.
Figure 5:
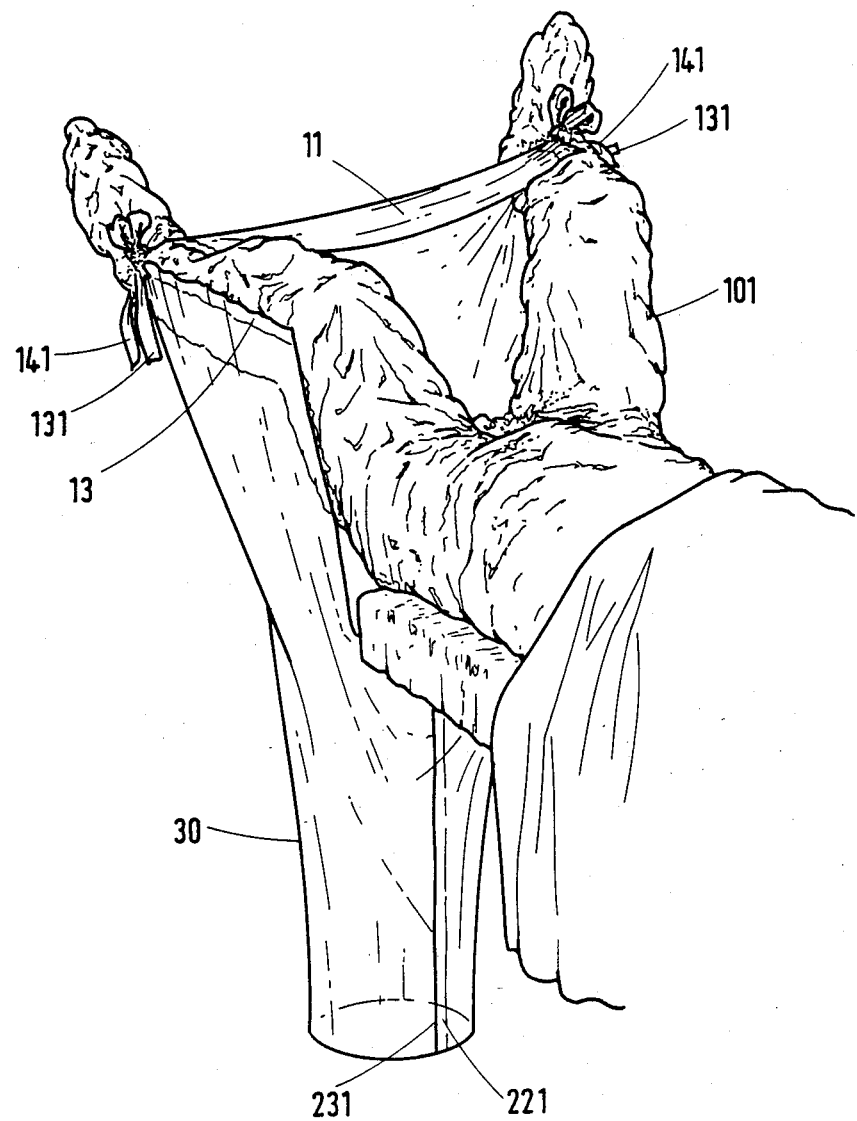
FIG. 5 is a perspective view of the arrangement using the form of drape shown in FIG. 2.

The embodiment illustrated in FIGS. 2 and 5 differes from that of FIG. 1 only in that the lower part 100 of the sheet is adapted to be formed permanently into a funnel by seaming together edge positions 221, 231 of the sides 22 23 of the lower portion of the sheet. The lower portion is of lesser width than in FIG. 1, because the required amount of overlap of the sides, 22, 23, when formed into a funnel, is less. The tapes 15 to 20 and hole 21 are omitted.

Figure 3:
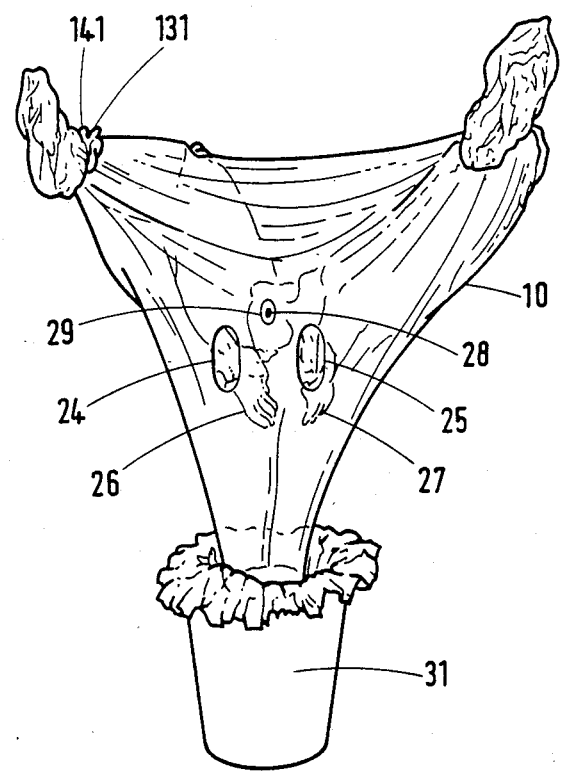
FIG. 3 illustrates the surgical drape of FIG. 1 attached to a patient in the lithotomy position,.
Figure 4:
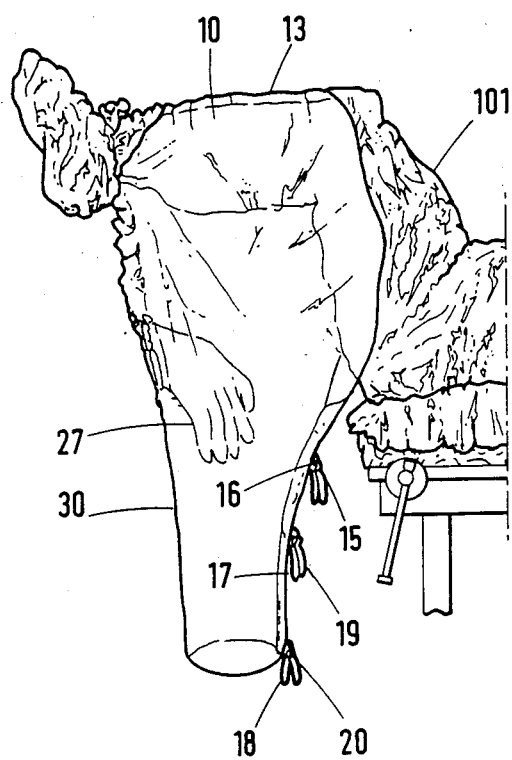
FIG. 4 is a side view of the arrangement of FIG. 3.

As shown in FIGS. 3, 4 and 5, in use the sheet 10 is attached at its upper edge 11 to the usual surgical covering 101 for the patient's legs by means of the tapes 131, 141, and self-adhesive strips 13, with the remainder of the sheet hanging down therefrom so as to protect the surgeon from body fluids emanating from the patient. In the embodiment of FIG. 1, tape 16 is passed through the hole 21 and tied to tape 15, thus drawing the lower part of the sheet into the form of a funnel 30 (FIGS. 3 and 4) with side 23 overlapping side 22, and it is held in this form by tying tapes 15 and 16, 17 and 19 and 18 and 20 together. A bucket 31 can be disposed to collect body fluids impinging on the sheet 10 and descending through the funnel 30, so as to maintain the operating environment in a clean condition. The surgeon can pass his hands through the apertures 24, 25 into the gloves 26, 27 and then manipulate the urological instrument (e.g. cytoscope) which is not shown in FIGS. 1 to 4.

In the embodiment of FIGS. 2 and 5, there is no need to use tapes to form the lower part of the sheet into the funnel 30, because the seaming of edge portions 221, 231 together pre-forms it into funnel shape, as seen in FIG. 5.

Figure 6:
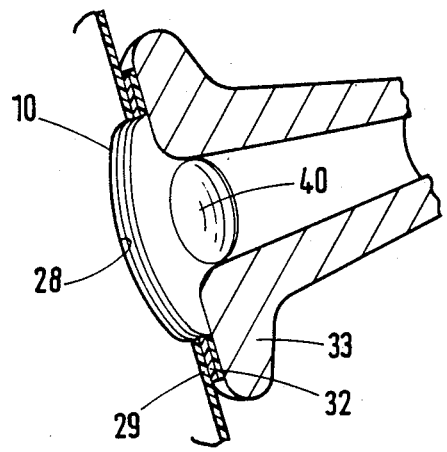
FIG. 6 is a diagrammatic sectional detail view, to a larger scale, showing the attachment of the lens casing of a urological instrument, such as a cystoscope, to the central sealable aperture of the surgical drape.
Figure 7:
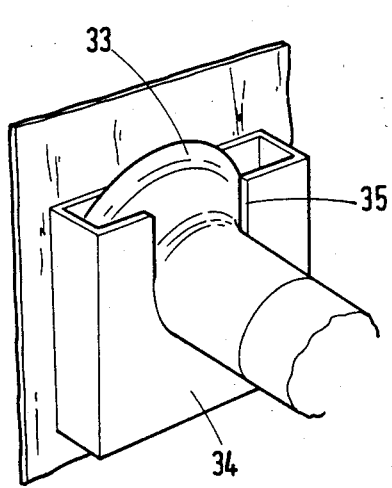
FIG. 7 is a detail view of a support for the lens of the urological instrument.
Figure 8:
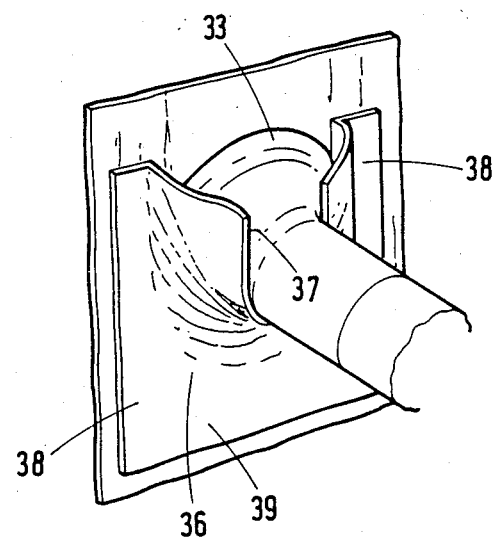
FIG. 8 is a similar view of a modified support.

FIG. 6 illustrates how the reinforcing ring 29 can be attached, e.g. by welding, to the sheet 10 around the aperture 28 and can also be attached by means of an adhesive ring 32 to the lens casing 33 of the cystoscope. The reinforcing ring 29 thus supports the lens casing 33. Further support is provided by a receptacle attached to the patient's side of the drape to receive and locate the lens casing 33. The receptacle may be either in the form of a rigid box 34 (FIG. 7) with a cut-out 35 in its rear side or in the form of a strong but flexible sheet 36 (FIG. 8) with a cut-out 37, attached around its side and lower edges 38, 39 to the sheet 10, e.g. by welding.

Figure 9:
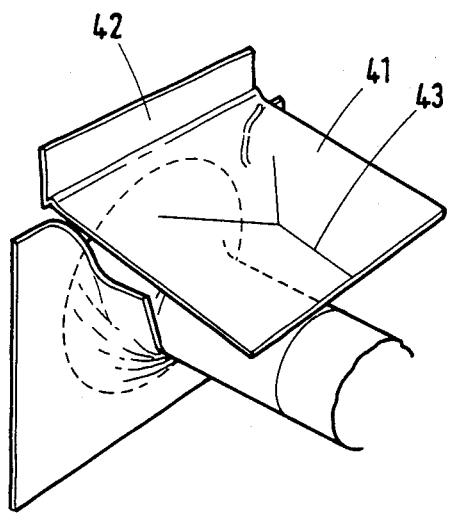
FIG. 9 illustrates a sealing flap for protecting the lens of the instrument.
Figure 10:
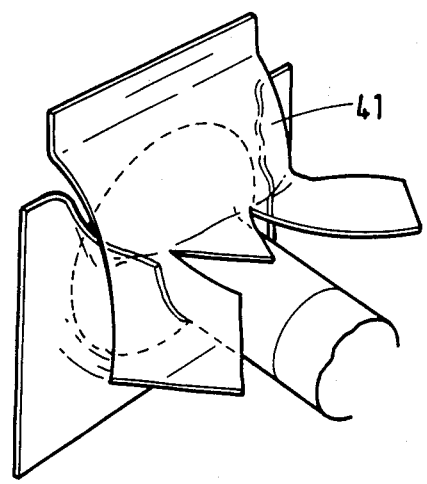
FIG. 10 illustrates the application of the sealing flap.
Figure 11:
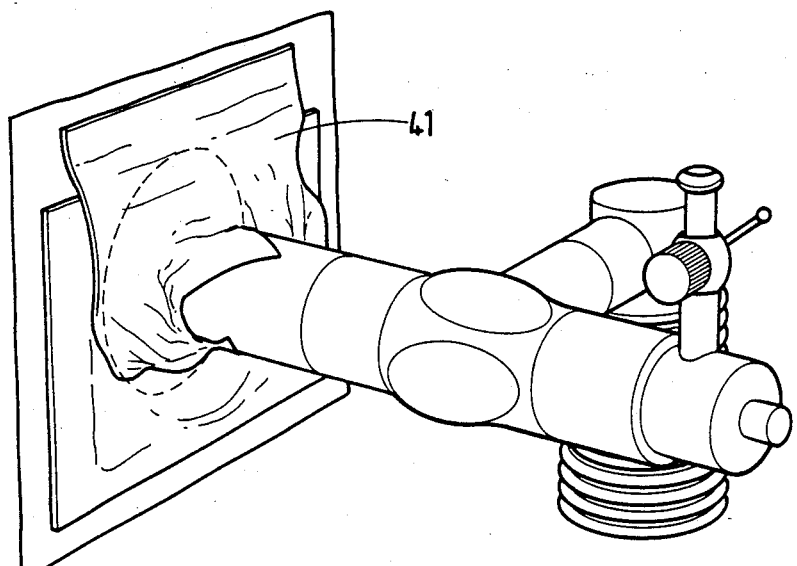
FIG. 11 shows the completion of the sealing of the lens.

The adhesive ring 32 shown in FIG. 6 seals the aperture 28 and protects the lens 40 of the cystoscope. To improve the sealing and protection, a self-adhesive flap 41 (FIGS. 9 to 11) may be welded along its edge 42 to the sheet 10 above the aperture 28 and provided with a Y-shaped cut 43. Prior to use the adhesive surface of the flap 41 would be covered by a liner (not shown). When the lens casing 33 has been inserted into the support provided by sheet 36, the liner is removed and the flap 41 is brought down as shown in FIG. 9 and wrapped around the lens casing as shown in FIG. 10, being finally adhered to the lens casing as shown in FIG. 11, thus effectively sealing the aperture 28 and protecting the lens 40.

An alternative form of rigid lens support is shown in FIGS. 12 and 13, comprising a fixed circular receptacle 45 with an annular rear wall 46 to be attached to the sheet 10 around the aperture 28, a front wall 47 having a cut-out 48 to receive the stem of the instrument (not shown) and a bottom wall 49 extending up to the horizontal diameter of the receptacle 45 on each side and provided with a drain hole 50. The support also comprises a top part 51 pivoted to the fixed receptacle 45 at 52 and comprising a front wall 53 with cut-out 54 and a top wall 55. In the position shown in FIG. 12, the lens casing of the instrument can readily be fitted into the receptacle 45, and on pivoting the top part 51 to the position shown in FIG. 13, the lens is protected from stray fluids.

The lens support of FIGS. 14 to 16 comprises a fixed receptacle 56 similar to that of FIGS. 12 and 13, and a movable cover portion 57 with an annular flange 58 fitting between fixed annuli 59, 60 which are secured to the sheet 10 at different radial distances from the aperture 28. In the open position, the fixed receptacle 56 can receive the lens casing 33, as shown in FIG. 15, and the movable cover portion 57 can then be rotated about the axis of the instrument to the closed position shown in FIGS. 16 and 17 in which the lens is protected.

Various changes may be made in the surgical drape within the scope of the invention. For example, a rigid lens support of the kind shown at 34 in FIG. 7 may be shaped to match the shape of the lens casing 33, and may be provided with a flexible protective flap like the flap 41.

Where the drape is to be used for gynaecological examination, the central aperture 28 may be replaced by a highly transparent inspection window sealed into the central part of the sheet 10.

In place of the surgical gloves 26, 27, the apertures 24, 25 may be closed by highly flexible elasticated membranes which permit the surgeon's hands to pass through the apertures.

For attaching the upper part of the sheet to the patient's legs, apertures may be provided in the upper part of the sheet to enable the patient's feet to be passed through them.

The surgical drape of the present invention enables the surgeon to carry out urological, gynaecological or proctorlogical surgical procedures or examinations in a convenient manner, while providing a hitherto unattainable protection from the patient's body fluids, and making it possible to keep the operating environment cleaner.

We claim:

1. A surgical drape for use in urological, gynaecological or proctorlogical surgical procedures or examination of patients, comprising a sheet of flexible transparent or translucent plastics material, one end of the sheet being provided with means for attaching the sheet to the patient's legs, so that the remainder of the sheet hangs down therefrom, the sides of the sheet in the region of the end remote from that provided with leg attachment means being provided with means to enable the sides to be joined, to form the remote region of the sheet into a funnel which is open at both ends, and a central part of the sheet being provided with apertures sealed by flexible members which permit passage of the surgeon's hands.

2. A surgical drape according to claim 1 wherein the central portion of the sheet is also provided with an aperture sealed by flexible members and also adapted to be sealed around an optical urological instrument thereby permitting ocular access to a lens of the urological instrument.

3. A surgical drape according to claim 2 wherein the central portion of the sheet has attached to it, around the sealable aperture, a support for the lens casing of the urological instrument.

4. A surgical drape according to claim 3 wherein the support is shaped to receive and locate the lens casing.

5. A surgical drape according to claim 1 wherein the central portion of the sheet is also provided with a highly transparent inspection window.

6. A surgical drape according to claim 1 wherein the flexible members permitting passage of the surgeon3 s hands are gloves sealed to the sheet around each aperture.

7. A surgical drape according to claim 1 wherein the flexible members permitting passage of the surgeon's hands are elasticated membranes sealed to the sheet around each aperture.

8. A surgical drape according to claim 1 wherein the means for attaching the sheet to the patient's legs comprise self-adhesive strips attached to the top edge of the sheet.

9. A surgical drape according to claim 1 wherein the means for attaching the sheet to the patient's legs comprise tapes capable of being tied around the legs.

10. A surgical drape according to claim 1 wherein the means for attaching the sheet to the patient's legs comprise apertures in the sheet through which the patient's feet can be passed.

11. A surgical drape according to claim 1 wherein the sides of the sheet adjacent to the lower end of the sheet are provided with attachment means in the form of at least one tape attached to one side and at least one hole adjacent to the other side to enable the tape or tapes to secure the sides in overlapping relationship and thereby form the lower part of the sheet into the funnel.

12. A surgical drape according to claim 1 wherein the sides of the sheet adjacent to the lower end of the sheet are provided with attachment means in the form of at least the tape attached to one side and at least one hole adjacent to the other side to enable the tape or tapes to secure the sides in overlapping relationship and thereby form the funnel.

13. A surgical drape according to claim 1, wherein the sides of the sheet adjacent to the lower end of the sheet are seamed together to form the lower part of the sheet into the funnel.

* * * * *